United States Patent [19]
Sandrock et al.

[11] 3,971,630
[45] July 27, 1976

[54] APPARATUS AND METHOD FOR BATCH-TYPE ANALYSIS OF LIQUID SAMPLES

[75] Inventors: Harold E. Sandrock, Rockville Centre; Edward W. Stark, Garden City, both of N.Y.; Steven A. Gyori, Allendale, N.J.

[73] Assignee: Technicon Instruments Corporation, Tarrytown, N.Y.

[22] Filed: Oct. 7, 1975

[21] Appl. No.: 620,462

[52] U.S. Cl. .......................... 23/230 R; 23/253 R; 23/259; 356/180; 356/197
[51] Int. Cl.² .................... G01J 3/46; G01N 21/24; G01N 33/16
[58] Field of Search .............. 23/230 R, 253 R, 259; 356/180, 184, 197

[56] References Cited
UNITED STATES PATENTS

| | | | |
|---|---|---|---|
| 3,549,330 | 12/1970 | Jungner et al. | 23/259 |
| 3,756,920 | 9/1973 | Kelbaugh et al. | 23/283 R X |

Primary Examiner—Robert M. Reese
Attorney, Agent, or Firm—S. P. Tedesco; Stephen E. Rockwell

[57] ABSTRACT

Apparatus and method for photometrically analyzing a constituent of interest in body or other fluids and well suited for kinetic determinations which are temperature-and-time dependent. There is provided a sample holder holding a cuvette supporting a liquid sample and other reactants among which is a trigger reactant to initiate the reaction which is analyzed. The trigger and the other reactants are initially isolated in the cuvette. The holder, one of a series, is moved periodically to move the cuvette, one of a series handled sequentially, to a temperature-sensing and preheating station, to a station where the contents of the cuvette are mixed to enable the reaction to proceed, to an optical station where the reaction is viewed for an optical density determination over a period of time under temperature conditions regulated within limits, and to a station for sensing the temperature of the mixture, by immersion of a temperature sensor therein, and supplying data for estimation of the real temperature during the optical determination for inclusion in the determination of the concentration of the constituent of interest, all in a relatively short period of time.

22 Claims, 8 Drawing Figures

APPARATUS AND METHOD FOR BATCH-TYPE ANALYSIS OF LIQUID SAMPLES

BACKGROUND OF THE INVENTION

1. Field of the Invention

This invention relates to apparatus and method for photometrically analyzing in batch type determinations the rate or end point of a chemical reaction for quantitation of a constituent of interest in a sample, usually blood serum.

2. Prior Art

Heretofore, manufacturers of fully automated photometric analyzers of the type designed to perform batch type enzyme quantitations of blood serum by kinetic or reaction rate measurements have sought unsuccessfully in moderate cost equipment to increase the number of samples analyzed per hour with reference to these temperature-and-time dependent reactions. This has posed the problem of getting the samples up to the proper temperature for the reaction and maintaining this temperature within very exacting, fine tolerances during the period of optical measurement, without contamination of sample. This problem may be termed one of sample incubation. For example, in the analysis of the enzyme CPK in blood serum it has been found that the concentration as determined by optical density may be off by as much as 8% for a deviation of 1.0°C from the set temperature such as 30°C or 37°C, for example. Exaggerated claims have been made by manufacturers concerning the fineness of the temperature regulation of sample in automated and semi-automated kinetic analyzers.

For diagnostic use in hospitals and laboratories where space is at a premium, it is desirable to automatically quantitate 30 or more samples an hour. It takes approximately 15 minutes supported in a cuvette in an air bath to bring the temperature from 4°C up to the temperature of 37°C of the liquid contents of approximately 1.5 ml of the cuvette. The cuvette with its serum sample, either with its reagents in freeze-dried condition or reconstituted condition, may have been taken from a refrigerator a short time before. An air bath of such loaded cuvettes is preferred to a water bath for optical reasons despite the advantage of the latter in tending to approach matching indexes of refraction and bring the liquid contents of the cuvette up to temperature in approximately 6 minutes if the water of the bath is well circulated. Such disadvantages are that the water of the bath requires replenishment from time to time, which may be overlooked by the operator. If the water level falls below the analyzer's viewing area, the analytical results are invalidated. Further, the bath water may have its temperature changed on replenishment. It may contain dirt which drifts between the optical window of the analyzer making it appear falsely to the photodetector, which detects change in the optical density of the sample mixture, that a change or shift in optical density has begun. Still further, impurities in the bath water coat such windows after a period of time and, hence, interfere with analysis. The use of such bath water is also cumbersome and inconvenient. On the other hand, if an equipment manufacturer relies solely on utilization of an air bath to reach and maintain a proper reaction temperature, at least initial severe and undesirable temperature gradients are established in the liquids and in the material of which the cuvette is structured, usually plastic. At least one manufacturer has attempted to avoid these problems by utilizing a closed pouch for the sample-reagent materials which are brought up toward design temperature by electrically heated plates placed temporarily in contact with the sides of the pouch. Such practice is open to the objection that the temperature of the liquid within the pouch is not sensed by a sensor inserted therein, and such plates may develop hot spots leading to the aforementioned undesirable temperature gradient.

In such kinetic determinations, the viewing area of the reaction within the cuvette must not be obscured by a temperature sensor. Yet, it is in this area that the temperature of the reaction mixture is most critical as the temperature of the liquid in another portion of the cuvette may be off by a few tenths of one degree, enough to invalidate many analyses if the total deviation is more than 1.0°C from the design or set temperature of 37°C or 30°C, for example. Another restriction in such analysis is that any temperature-sensing probe immersed in the liquids of cuvettes successively must not contaminate, by sample and/or reagent carryover from one cuvette to the next, the reactants. Further, as far as is known, no automated kinetic analyzer has existed heretofore which goes beyond the sample liquid temperature-regulating limitations of the equipment design in computing the constituent concentration, that is, to the estimated real temperature at the time of the optical determination for inclusion in the concentration determination.

The present invention seeks to overcome these difficulties with the prior art.

SUMMARY OF THE INVENTION

One object of the invention is to provide improved apparatus and method for photometrically analyzing a constituent of interest in body or other fluids by an end point quantitation or by a kinetic determination. Another object is to provide in such an analyzer fully automated analysis from the point of introduction into the analyzer of a cuvette loaded with the liquid sample, usually blood serum, and the necessary reactants. A further object is to provide in such analyzer a closely regulated thermal environment for the contents of the cuvette in which there is improved preheating of the liquid contents, and wherein the real temperature of the mixture at the time of the viewing of the reaction is estimated for inclusion in the determination of concentration of the constituent of interest.

Still further, there is provided a sample holder holding a cuvette supporting a liquid sample and the other reactants among which is a trigger reactant to initiate the reaction which is analyzed. The trigger and the other reactants are initially isolated in the cuvette. The holder, one of a series, is moved periodically to move the cuvette, one of a series handled sequentially, to a temperature-sensing and preheating station, to a station where the contents of the cuvette are mixed to enable the reaction to proceed, to an optical station where the reaction is viewed for an optical density determination over a period of time under temperature conditions regulated within limits, and to a station for sensing the temperature of the mixture, by immersion of a temperature sensor therein, and supplying data for an estimation of the real temperature during the optical determination, all in a relatively short period of time.

DETAILED DESCRIPTION OF THE PREFERRED EMBODIMENTS

Figure 1:
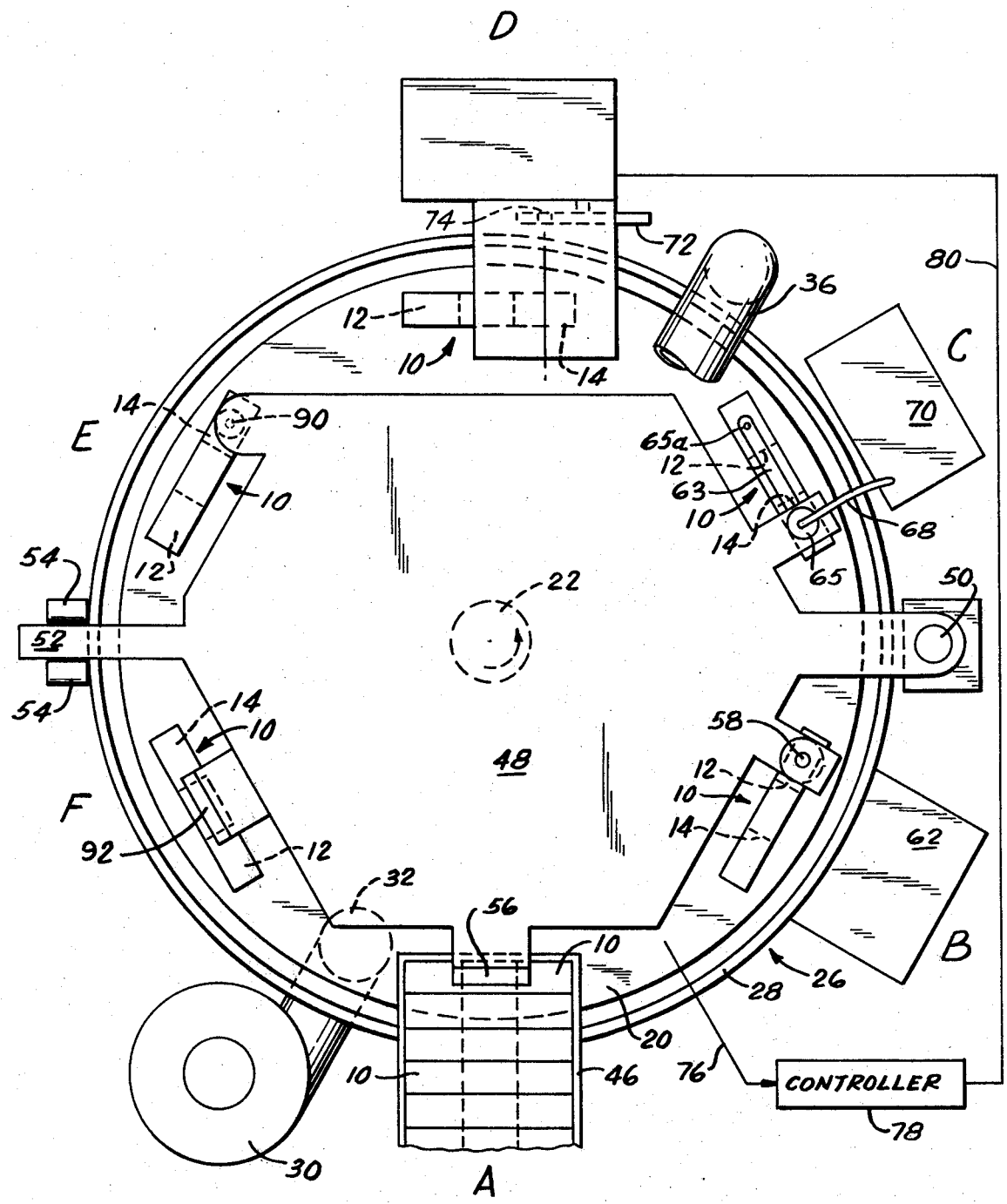
FIG. 1 is a fragmentary schematic plan view of the photometric analyzer embodying the invention, omitting the outer housing and the inner cover.

In FIG. 1 there is shown the general organization of the photometric analyzer having in circular array a cuvette loading station A; a staton B for preheating the liquid contents of a cuvette under the control of a temperature-sensing probe immersed in such contents; a station C where certain of such liquid contents, previously maintained in isolated condition, are mixed; a station D at which the reaction resulting from such mixture is measured optically; a station E at which a temperature-sensing probe is immersed in the liquid contents in the optical chamber for the determination of the then temperature of such contents for estimation of the temperature of such contents when previously at station D, during such optical measurements, obtained by backward extrapolation for inclusion in the concentration determination; and a station F where the cuvette is ejected for disposal from the operating portion of the analyzer.

Figure 2:
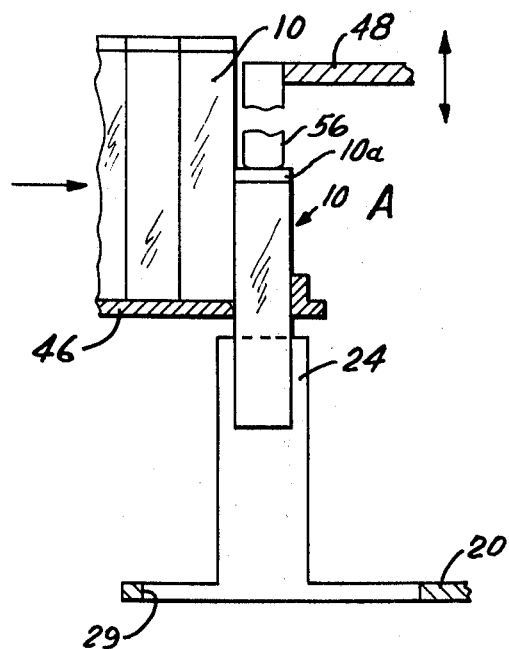
FIG. 2 is a fragmentary, schematic elevational view, partially in section, illustrating station A of the analyzer of FIG. 1.
Figure 4:
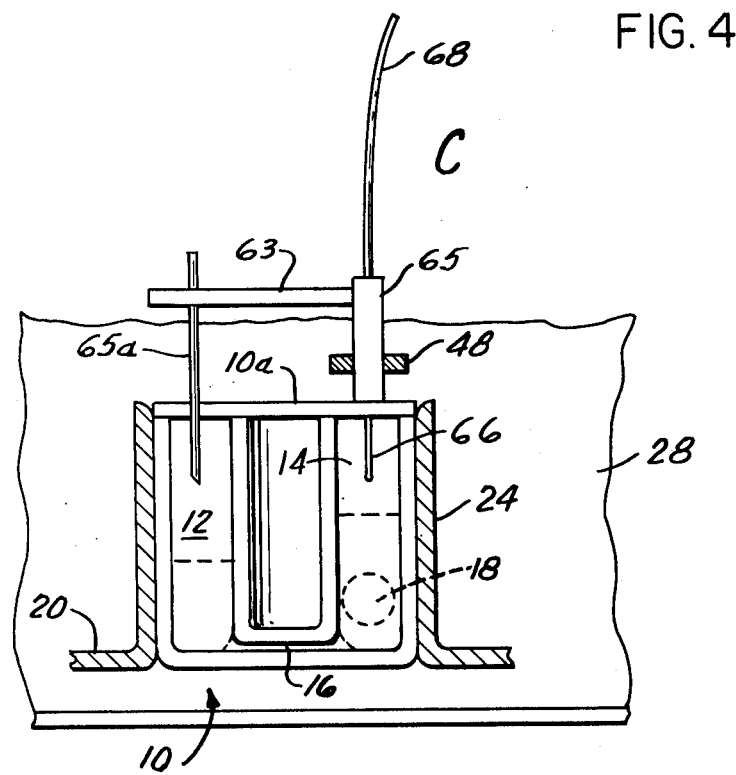
FIG. 4 is a similar diagrammatic view illustrating station C of the analyzer of FIG. 1.

The cuvette is one of a series of such cuvettes indicated generally at 10 and best shown in FIGS. 1, 2 and 4. Each cuvette 10 has a probe-puncturable cover 10a. As shown in the last-mentioned view, each cuvette 10 has a minimum of two chambers 12 and 14, either of which may hold the trigger reagent or the other reagent and either of which may also contain the blood serum sample, such reactants being in liquid form. The last-mentioned chambers may be placed in liquid-flow communication with one another selectively or on demand by any one of a number of ways illustrated and described in the copending U.S. patent application of Sandrock et al, Ser. No. 604,526, filed Aug. 27, 1975. In the form illustrated in FIG. 4, the chambers 12 and 14 have therebetween a capillary passageway 16 normally devoid of liquid and maintaining the respective liquids in isolated condition by surface tension and/or an air lock in the passageway which may be overcome for mixing of such contents by gas such as air supplied under pressure to one of the chambers which will be described in detail hereinafter. The cuvette has a pair of opposed optical windows, one of which is shown at 18, in the chamber 14 in the illustrated form. The chamber 14 is the optical chamber for analysis of the reaction mass contained therein, the optical path through which mass is generally defined by such windows of the chamber.

With reference to the aforementioned stations of the analyzer, it may be important in some analyses that no probe be immersed in the liquid contents of the chamber 14 until after the optical measurements have been made at station D. The reasons are twofold. First, the cuvettes 10 are loaded one after another at station A into successive holders in fixed circular array on a carousel 20 periodically moved angularly on a motor driven shaft 22, one such holder being shown to advantage in FIG. 4 and indicated at 24. The cuvettes are operated upon successively and periodically by probes extended through the cuvette covers 10a at various aforementioned analyzer stations. Hence, there is a risk, unless avoided as in the instant invention, of contaminating carryover of sample and reagent by a probe between the chamber 14 of any one cuvette and the chamber 14 of the next following cuvette, and where such contamination is a problem no probe is immersed in the liquid contents in the reaction chamber 14 until the cuvette reaches station E after the aforementioned optical measurement. Secondly, the horizontal cross section of the optical chamber 14 is relatively small measuring approximately 0.8 cm × 1.0 cm, and if a temperature sensing probe were to be immersed in such chamber during such optical measurements such probe might obscure the optical path between the windows of the chamber 14. As previously indicated, a feature of the invention resides in essentially establishing the real temperature of the reaction mixture in the optical chamber at the time of the optical measurement for inclusion in the calculation of the concentration of the constituent of interest in the sample.

Figure 3:
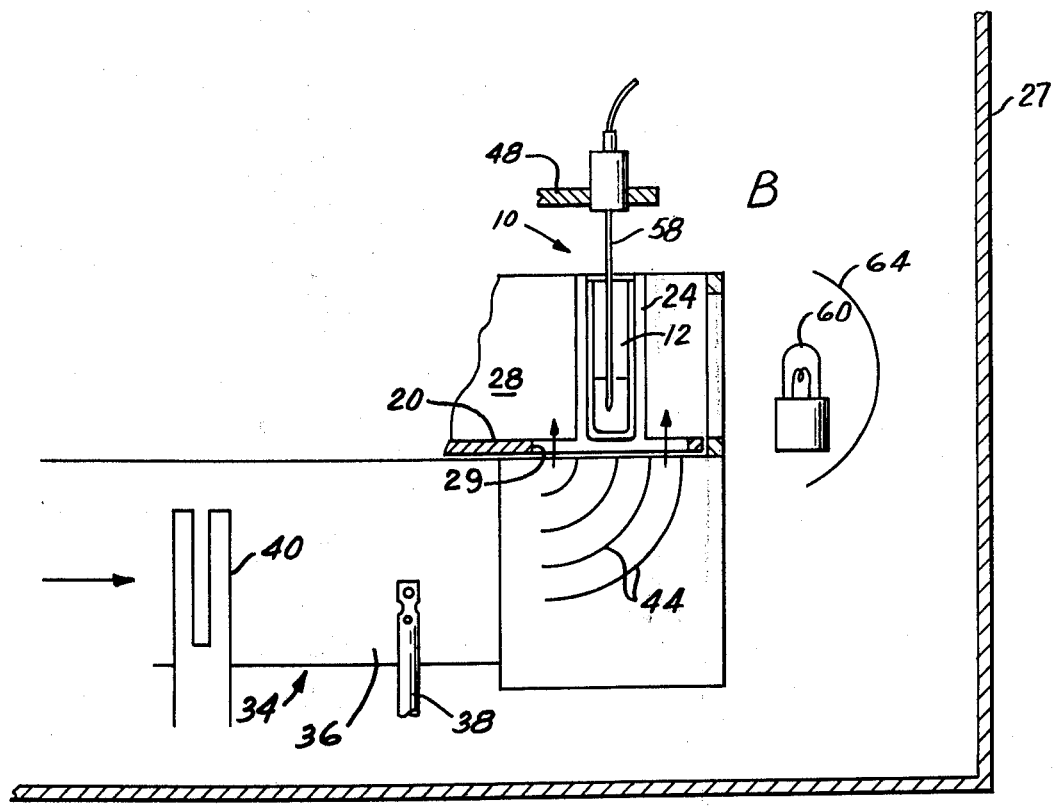
FIG. 3 is a fragmentary, elevational view partially in section and illustrating somewhat diagrammatically station B of the analyzer of FIG. 1.

The carousel 20 is disposed within a circular inner housing 26 having an upstanding sidewall structure 28. A nonillustrated inner cover is provided for the housing 26 and a blower 30 introduces air, as at 32 (FIG. 1), into the lower portion of the housing through a plenum portion 34 thereof, best shown in FIG. 3, which plenum underlies all the aforementioned stations, except station F, and has upward outlets in the area of the respective cell holders when at the other respective stations. The outlet from the plenum at station B is illustrated in FIG. 3. As shown in this view, the carousel 20 is cutaway, as at 29, for upward flow of air around the cuvette 10 in the holder 24. Such upward circulation of air passes through the center of the nonillustrated inner cover into an outlet 36 for recirculating the air to the blower 30 in a conventional manner.

As shown in the last-mentioned view the plenum includes a horizontal duct 36. The recirculating air stream is temperature controlled by a nonillustrated time-proportional, reset-action temperature controller. The air temperature is sensed by a thermistor 38 before upward discharge around the cuvette 10 at station B. The air heating is obtained by a low mass, wire wound heater 40 which responds quickly to any thermal load change. The returning air is passed over the heater 40 and mixed by a circulating fan, not shown. To achieve uniform air velocity and temperature distribution around the cuvette 10 and minimize pressure drops in the air system, turning vane flow directors 44 are employed. In this view, the outer housing is indicated at 27. The general construction of the carousel 20, housing 26 and the plenum portion 34 thereof, together with the aforementioned associated elements thereof, will be understood from the foregoing.

As shown in FIGS. 1 and 2, at station A the housing is apertured through the sidewall 28 thereof to receive a magazine 46 supported in a conventional manner and having an opening through the bottom thereof for discharge therethrough, one at a time, of a cuvette 10 into the particular cuvette holder 24 in registration therewith. The injection of the cuvette into the holder 24 of the carousel as shown in FIG. 2 is accomplished through an actuator 48 which performs functions at all the aforementioned analyzer stations, except station D. The actuator 48 is of horizontally extending, generally plate-like construction located above the carousel 20 and intermittently movable up and down on a power driven rod 50 (FIG. 1). The actuator 48 has a laterally extending guide projection 52 coacting with guide elements 54 on opposite sides thereof. The actuator 48 has fixed thereto a depending plunger 56 to engage the top of the cuvette 10 to be injected by the plunger at the station A on downward movement of the actuator 48 as shown in FIG. 2. On injection into the cuvette holder at station A, the cuvette is subjected to the aforementioned air bath. The cuvette is loaded into the carousel while the latter is stationary. The carousel 20 is moved angularly one increment, that is one station, periodically, say every two minutes for example, by the motor driven shaft 22 when the actuator 48 is in the up position. When the first injected cuvette 10 reaches station B on the movement of carousel while the actuator 48 is in its up position, the actuator 48, after the carousel movement has stopped, is moved downwardly to inject the next following cuvette 10 in the magazine 46 into the next following holder 24 of the carousel then in registry with the station A. The cuvettes in the magazine 46 are engaged flatwise with one another in the manner illustrated in FIGS. 1 and 2 and are biased in a suitable manner toward the point of injection into the carousel.

On the last-mentioned downward movement of the actuator 48, a depending thermistor probe 58 fixed thereto is extended through the cover 10a of the cuvette positioned at station B and immersed in the liquid of the chamber 12 for sensing the temperature thereof, as shown in FIG. 3. The air bath and the preheating of the cuvette contents at station B may be set to elevate the temperature of the liquid contents to within ± 1.0 of 37°C, or if desired of 30°C, by the time the cuvette reaches station D. Under the control of the probe 58 a tungsten-halogen lamp 60 is energized in the housing 62 (FIG. 1) which conforms to the outer contour of the sidewall structure 28 and is fixed thereto. The housing 62 extends over an opening (FIG. 3) in such sidewall structure in registry with the lamp 60, and a paraboloid mirror reflector 64 focuses the lamp on the liquid contents of the cuvette at station B. The lamp 60 is chosen to radiate energy the major component of which is in the infrared region of 1.46 microns, for example, at which the material of the cuvette, usually plastic, is essentially transparent so that approximately 80% of such radiation is absorbed by the liquid. The thermistor probe 58 is preferably gold plated and may have the outer shape and dimensions of a hypodermic needle to puncture the cover 10a of the cuvette. The gold plating prevents direct infrared radiation pick-up by the sensor. Therefore, the sensor 58 is activated primarily by the liquid temperature. The temperature rise in the liquid contents of the cuvette under the influence of the lamp 60 is essentially uniform and without temperature gradients. On the liquid contents reaching the set temperature, the lamp 60 is deenergenized and the circulating air maintains the temperature of the cuvette contents. It is to be understood that the lamp 60 is energized only if the immersed probe 58 senses a temperature below that for which the analyzer is set. The cuvette is maintained at station B for two minutes in the form illustrated by way of example. At the expiration of this interval the actuator is again raised to its up position, withdrawing the sensing probe 58, and the carousel is moved angularly one increment to bring the last-mentioned cuvette in registry with station C.

When the actuator 48 again descends, another cuvette is injected into the carousel at station A, and at staton C, shown in FIG. 4, a tubular probe 66 depending from and fixed to the actuator 48 punctures the cuvette cover and extends into the chamber 14 without being immersed in the liquid therein so as to avoid contamination thereof in the manner shown in FIG. 4. Simultaneously, a tube 65a open at both ends, supported on an arm 63 from the probe support 65, punctures the cover 10a to extend into the chamber 12 above the liquid level therein to vent the last-mentioned chamber. A flexible tube 68 (FIG. 1) is coupled between the probe 66 and a pump 70 which is energized when the actuator 48 descends. The pump 70 alternately delivers air under pressure to the chamber 14 and creates a partial vacuum therein in what may be termed one cycle of the mixing operation which effectively places the chambers 12 and 14 in liquid-flow communication by breaking the surface tension of the liquids at the ends of the passageway 16 shown in FIG. 4 and any air lock in such passageway. Sixteen cycles of such mixing action may be sufficient to mix the contents of such chambers. In the present example, the cuvette remains at mixing station C for an interval of two minutes.

Figure 5:
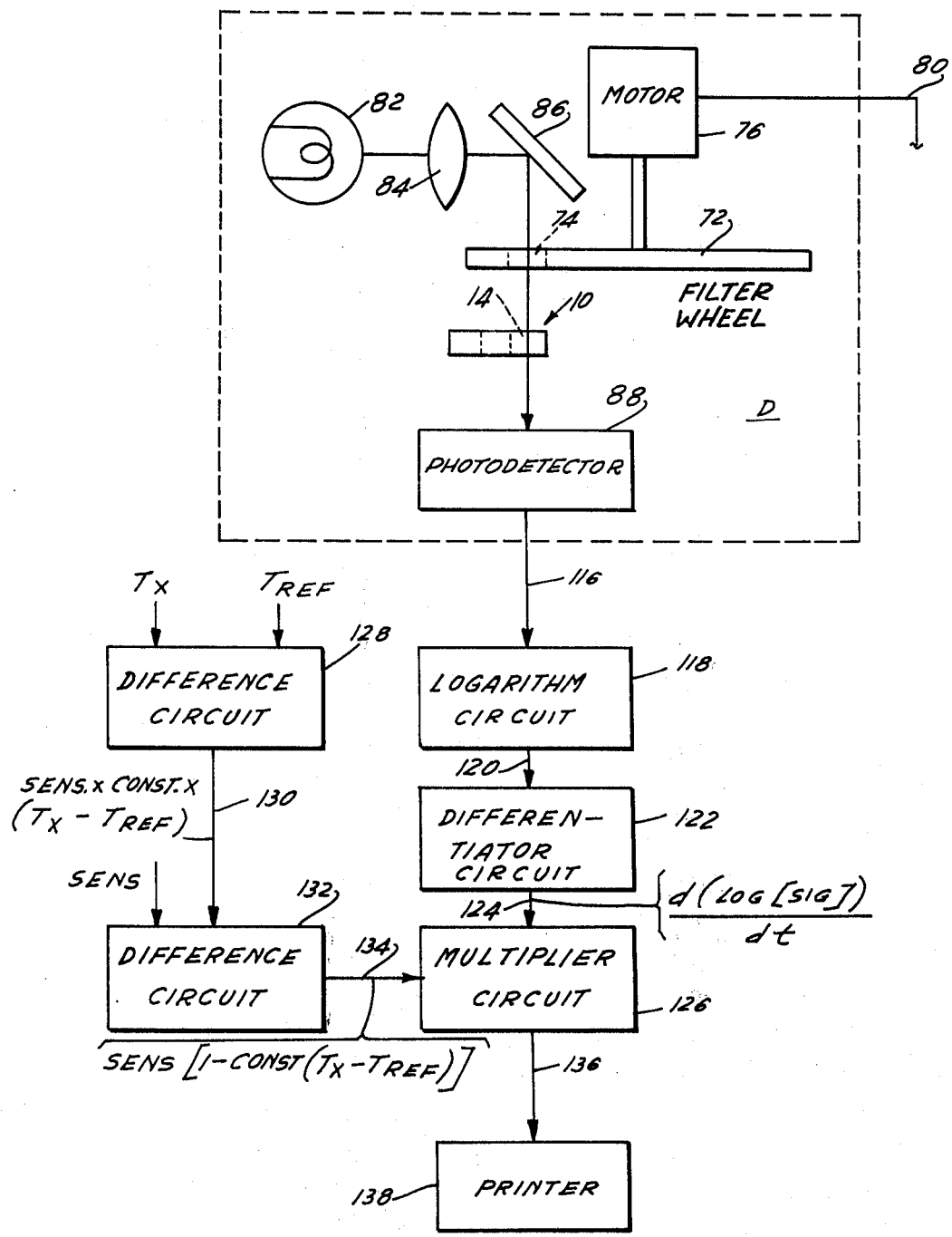
FIG. 5 is a similar diagrammatic view illustrating station D of the analyzer of FIG. 1 with an accompanying block diagram of a portion of the data processing circuitry.

At the end of this interval the actuator is again raised to its up position and the carousel is indexed one increment to place the last-mentioned cuvette in registry with the optical station D, while another cuvette is loaded into the carousel at station A. As best shown in FIG. 5, the optical station D includes a filter wheel 72 having a circular array of filters, one being shown at 74, the wheel being driven by a motor 76 energized periodically from a controller 78 through lead 80 as shown in FIG. 1. Each cuvette bears nonillustrated indicia thereon such as a code to indicate to a nonillustrated conventional code reader the particular test and the filter or filters required for optical measurements of the contents of that cuvette at the optical station D. Preferably the code is read on the fly as the cuvette moves from station A to station B and is located at the position shown by the arrow 76 in FIG. 1. The output from the reader is to the controller 78 as shown. The actuator 48 as shown does not extend over any portion of the optical station D which straddles the cuvette at station D. As shown in FIG. 5, the station D includes a lamp 82, a focusing lens 84 and a mirror 86 to reflect a beam of light from the lamp at a 90 degree angle through the filter 74 and through the windowed optical chamber 14 upon a photodetector 88. During the two minute interval that the last-mentioned cuvette is at D, 108 readings may be made at 0.5 second intervals for example, utilizing one filter or two filters, one at a time, of different wavelengths. Prior to discussing the processing of data from the signals delivered by the photodetector 88, the remainder of the apparatus shown in FIG. 1 will be described.

Figure 6:
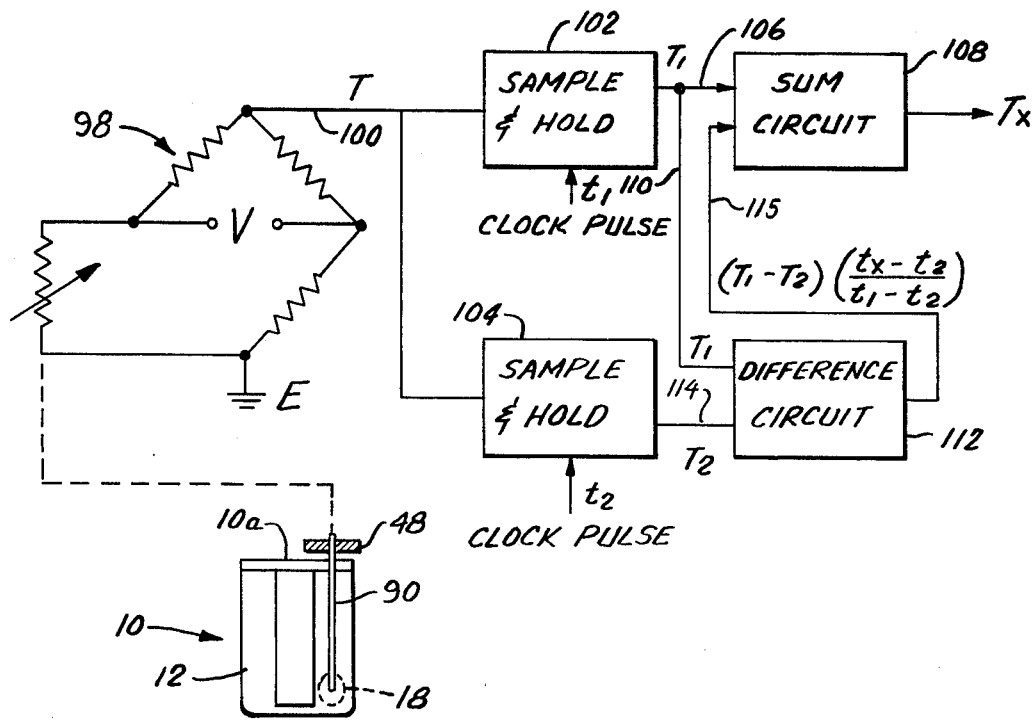
FIG. 6 is a diagrammatic view illustrating station E of the analyzer of FIG. 1 with an accompanying portion of the data processing circuitry which circuitry has delayed output to the circuitry of FIG. 5.

Upon the actuator 48 next reaching the up position thereof, the carousel is again rotated one increment to place the last-mentioned cuvette at station E at which the actuator 48 has a fixed depending thermistor probe 90 for immersion in the liquid in the optical chamber 14 of the cuvette upon the next downward movement of the actuator as another cuvette is loaded into the carousel at sttion A. The probe 90 and associated parts are best shown in FIG. 6. On the last-mentioned movement, the probe 90 punctures the cover 10a of the cuvette 10 for such immersion. The last-mentioned cuvette is at station E for 2 minutes and during this interval two temperature samplings are taken at time $t_1$ and $t_2$. The processing of these samplings will be discussed hereinafter.

Figure 8:
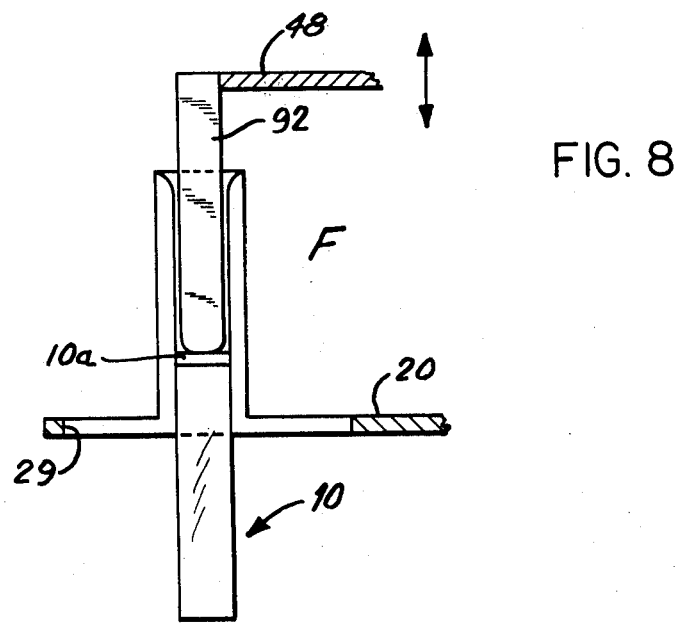
FIG. 8 is a fragmentary diagrammatic view illustrating station F of the analyzer of FIG. 1.

When the actuator 48 is again in raised position, the carousel 20 is angularly moved one increment to place the last-mentioned cuvette at the station F. When the actuator 48 next descends it ejects the cuvette by a plunger 92 (FIG. 8) fixed thereto engaging the top of the cuvette, for convenient disposal, not shown, of the cuvette with its contents. It is to be understood that as the cuvette is ejected at station F, a cuvette from magazine 46 is injected into the carousel at station A, and that when the actuator 48 is again in raised position the cuvette holder 24 of the carousel at station F is shifted on the next incremental movement of the carousel to bring this holder 24 to station A, the carousel having moved full circle. The aforementioned operation on each cuvette loaded into the carousel may continue with replacement cuvette magazines being supplied as needed.

Figure 7:
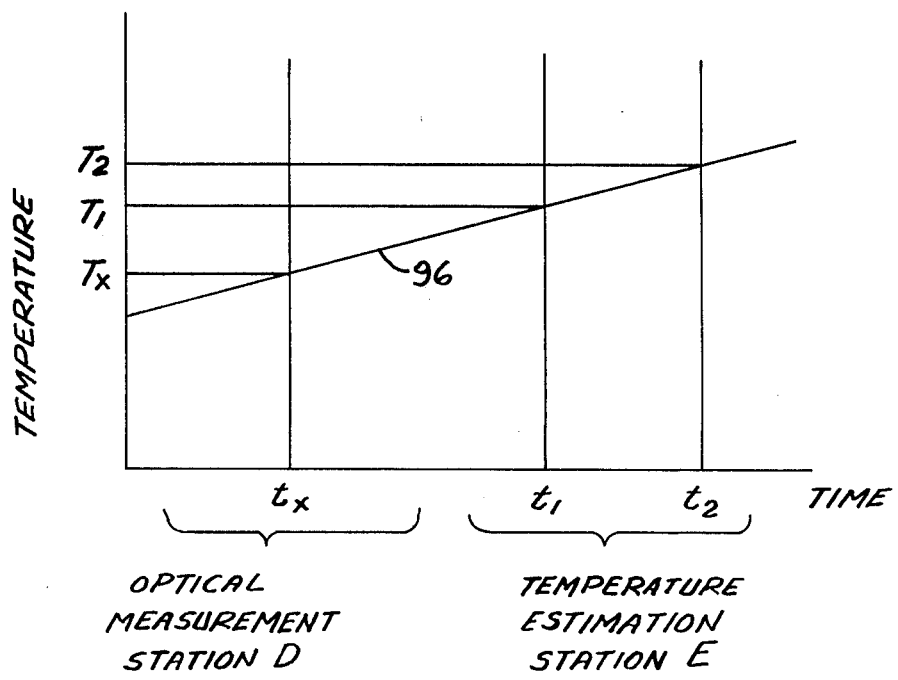
FIG. 7 is a graphic view illustrating the function of station E.

Turning now to the data processing circuitry of FIGS. 5 and 6 and first to the circuitry of FIG. 6, T indicates temperature as a function of voltage, $T_1$ is the temperature at time $t_1$ and $T_2$ is the temperature at time $t_2$. $T_x$ is the estimated real temperature of the reaction mixture at the mid-point in time of the optical readings of the reaction mixture at station D. The estimation of such temperature is graphically shown in FIG. 7 wherein $t_x$ indicates the time at which temperature $T_x$ is estimated. As shown in the last-mentioned view it is assumed that the temperature shift along the slope 96 between time $t_x$ and $t_2$ is linear. This assumption is essentially warranted owing to the fact that the temperature shift between time $t_x$ and $t_2$ is only a few tenths of a degree, and as the times $t_1$ and $t_2$ of sampling the temperature in the chamber 14 of the cuvette, which may be governed in a conventional way from a nonillustrated clock, are of preferably equal distance in time to each other and to the beginning and end, respectively, of the two minute interval of residence of the cuvette at station E. As shown in FIG. 6, the temperature sensing probe 90 includes a variable resistor of a Wheatsone bridge, indicated generally at 98, which has a voltage output as a function of temperature along lead 100 to each of sample-and-hold circuits 102 and 104. Circuit 102 has a clock pulse input at time $t_1$ and circuit 104 has a clock pulse input at time $t_2$, each for sampling the liquid temperature in the chamber 14. Circuit 102 has an output $T_1$ along the lead 106 to one input of sum circuit 108 and also such output along lead 110 to one input of difference circuit 112. Circuit 104 has an output $T_2$ along lead 114 to the other input of difference circuit 112. The output of circuit 112 along lead 115 to the other input of the sum circuit 108 is of the character indicated in FIG. 6. The output of circuit 108 is $T_x$. The value $T_x$, obtained by extrapolation, has an input to the data processing circuitry of FIG. 5 as will appear hereinafter. The concentration of the constituent of interest of the sample as determined by the last-mentioned circuitry is a function in part of $T_x$.

As shown in FIG. 5, the signal outputted from the photodetector 88 at the optical station D along lead 116 is to logarithm circuit 118 which has an output along lead 120 in the form of a logarithm of the signal to differentiator circuit 122. The signal received by the circuit 122 is then differentiated to obtain the derivative with respect to time, expressed as shown in FIG. 5, which is outputted along lead 124 to multiplier circuit 126. Except for inclusion of the estimated temperature, the derivative is proportional to the concentration of the constituent of interest of the sample under analysis. The constant of proportionality is termed the "sensitivity" (herein abbreviated as "SENS."), and is defined as the ratio of the concentration to the derivative of the logarithm of the signal.

The delayed inclusion of the estimated temperature $T_x$ is performed by first differencing the temperature $T_x$ and reference temperature, $T_{REF}$. As shown in FIG. 5, $T_x$ goes to one input of difference circuit 128, while the temperature at which the analyzer is set, $T_{REF}$, say 37°C, is inputted to the other input of circuit 128. The output of the circuit 128 along lead 130 is scaled such that the difference is multiplied by a constant (hereinafter abbreviated as "CONST.") equal to the SENS. multiplied by the temperature coefficient and expressed as shown in FIG. 5. This difference is applied along the aforementioned lead 130 to an input of a second difference circuit 132. SENS., a constant, is inputted to a second input of the circuit 132. The difference obtained by the circuit 132 and outputted along lead 134 to multiplier circuit 126 equals the product of SENS. and the estimated temperature factor, and this is then multiplied in the circuit 126 with the input from the differentiator circuit 122. The product is the concentration of the constituent of interest of the sample. This is outputted along lead 136 to a printer 138 which prints out the result.

As previously indicated, the cuvettes 10 are fed into the carousel 20 sequentially, one being injected into the carousel as another is ejected for disposal. Samples are analyzed at a rate of one every two minutes in this example. Also, in this example, one incremental movement of the carousel may take between 3–8 seconds. Further, under the control of the code reader through the controller 78, the optical reading at station D may be either an end point detection or a kinetic determination, depending on the code on the cuvette. Still further, if desired the station B may incorporate an optional pre-mixing feature for mixture of the cuvette contents.

One example of the risk of reagent carryover from one cuvette to another is in the analysis in one cuvette of LDH immediately following the analysis in another cuvette of SGPT. In the analysis of the latter, LDH is employed as a reagent in chamber 14. If the temperature sensing probe 90 were to be immersed in the cuvette containing the reagent LDH and then into the next cuvette prior to or during optical measurements of LDH, it would contaminate the last-mentioned cuvette by carryover of LDH and invalidate the analysis for LDH. However, if random analyses for constituents of interest of serum samples are not required and the sequence of analyses maybe predetermined, and if there is no risk of prejudicial sample and/or reagent carryover, the equivalent of the probe 90 may be immersed in the liquid mixture in the chamber 14 prior to the optical measurement for the purpose of estimating the real temperature of such mixture during such measurement.

A typical use of the analyzer is the quantitative determination of the enzyme lactic dehydrogenase (LDH) in a sample of blood serum. The reagents employed are lactic acid, the key component or trigger for the reaction, nicotinamide adenine dinucleotide (NAD) with an appropriate buffer (tris [hydrozymethyl] amino methane) in order to maintain pH. When these reagents are mixed in the presence of the sample as in a cuvette 10, any lactic dehydrogenase in the sample acts as a catalyst which catalyzes the reaction to form as reaction products pyruvic acid and NADH. Since NADH has a substantially higher optical density than does NAD, the rate of any increase in optical density is a function of the amount of the enzyme lactic dehydrogenase in the sample. The reaction may be optically measured at a wavelength of 340 nm.

While the presently preferred embodiments of the invention have been described, it will be apparent, especially to those versed in the art, that the invention may take other forms and is susceptible to various changes in details without departing from the principles of the invention.

What is claimed is:

1. An analyzer for a constituent of interest in a liquid sample, comprising: means defining a chamber, means regulating within limits the thermal environment within said chamber of contents within a container including said sample and at least one reagent, means determining the optical density of said contents in said container within said chamber within said limits and subsequent to the combination of said contents, means sensing the temperature of said contents in said container at a time other than during said determination and generating a signal in response thereto, and means responsive to said signal for extrapolating the real temperature of said contents at the time of said determination as a function of the quantitation of said constituent of interest.

2. Apparatus as defined in claim 1, wherein: said temperature-sensing means is within said chamber.

3. Apparatus as defined in claim 1, wherein said temperature-sensing means comprises a probe immersed in said contents.

4. Apparatus as defined in claim 1, wherein: said temperature-sensing means is immersed in said contents subsequent to said optical determination.

5. Apparatus as defined in claim 1, wherein: said container comprises at least two liquid holding chambers one of which is optically windowed for said determination, and said temperature-sensing means comprises a probe immersed in said optical chamber only subsequent to said determination.

6. Apparatus as defined in claim 1, wherein: said sample is one of a series of samples supported in respective containers, said determining means comprising means successively determining the optical density of said contents of said containers, said sensing means comprising means sensing the temperature of said contents of said containers successively to generate a signal for each one, and said signal-responsive means extrapolating the real temperature of said contents for each of said determinations.

7. A method for analyzing a constituent of interest in a liquid sample, comprising the steps of:
placing a container with its contents of such sample and at least one reagent in a chamber;
regulating the thermal environment within said chamber within limits;
determining the optical density of said contents within said container within said chamber subsequent to the combination of said contents;
sensing the temperature of said contents at a time other than during said determination and generating a signal in response thereto; and
extrapolating in response to said signal the real temperature of said contents at the time of said determination.

8. A method as defined in claim 7, wherein said temperature sensing is within said chamber.

9. A method as defined in claim 7, wherein: said sample is blood serum.

10. A method as defined in claim 7, wherein: said sample is one of a series of samples supported in respective containers, said placement step comprising placing said containers in said chamber, said optical determination comprising determining successively the optical density of said contents of said containers, said sensing step comprising sensing the temperature of said contents of said containers successively to generate a signal for each one, and said signal-responsive extrapolating step comprising extrapolating the real temperature of said contents for each of said determinations.

11. A method as defined in claim 7, wherein: said sensing of the temperature is by immersing a probe in said contents.

12. A method as defined in claim 11, wherein: said temperature sensing is subsequent to said determination.

13. A method as defined in claim 11, wherein: said probe is immersed in said contents only subsequent to said determination to generate said signal.

14. An analyzer for a constituent of a fluid sample, comprising: means defining a chamber, means circulating a thermally regulated gaseous bath in said chamber for thermal treatment of contents within a container therein including such sample and at least one reagent, means within said chamber for sensing the temperature of said contents, and radiant heating means within said chamber responsive to said sensing means for heating said contents within said container.

15. An analyzer as defined in claim 14, wherein: said sensing means comprises a probe for immersion in said contents.

16. An analyzer as defined in claim 14, wherein: said radiant heating means comprises a radiant lamp and a focusing reflector, said lamp being energized and deenergized in response to said sensor.

17. An analyzer for a constituent of interest in a liquid sample supported in a first chamber of a container having a second chamber containing a liquid reagent, said container normally isolating said reactants and selectively enabling fluid flow between said chambers one of which is an optical chamber, comprising: a container holder relatively movable along a predetermined path to each one of plural function-performing means, and means to relatively move said holder to each one of said plural means, one of said plural means comprising a temperature-sensing probe for immersion in said reactant of one of said chambers, another of said plural means comprising means for relative extension into the other of said chambers short of said reactant therein for establishing fluid flow between the chambers and mixing of said reactants, and another of said plural means comprising means determining the optical density of the product of such mixture in said other chamber which is said optical chamber.

18. Apparatus as defined in claim 17, wherein: said means comprising said temperature-sensing probe comprises means regulating the temperature of said reactants.

19. Apparatus as defined in claim 17, wherein: said means for relative extension into said other chamber comprises a tubular probe delivering gas under pressure.

20. Apparatus as defined in claim 17 wherein: said sample is one of a series of such samples supported in one of a series of such reagent-carrying containers, said container holder being one of a series of such container holders movable relatively successively along said path, and said means to relatively move said said holder relatively moves said holders to each one of said plural means.

21. Apparatus as defined in claim 20 further including a magazine holding said containers and means to feed said containers from said magazine sequentially into holders in registry therewith.

22. Apparatus as defined in claim 20, wherein: said holders are in fixed circular array on a carousel.

\* \* \* \* \*